United States Patent
Weber

(10) Patent No.: US 11,883,270 B2
(45) Date of Patent: Jan. 30, 2024

(54) METHOD FOR DETERMINING AND/OR VISUALIZING AIRFLOW THROUGH ABSORBENT CORES AND ABSORBENT ARTICLES EXHIBITING ENHANCED AIRFLOW

(71) Applicants: ONTEX BV, Buggenhout (BE); ONTEX GROUP NV, Erembodegem (BE)

(72) Inventor: Ainas Weber, Bad Neuenahr-Ahrweiler (DE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 621 days.

(21) Appl. No.: 17/254,909

(22) PCT Filed: Jun. 29, 2018

(86) PCT No.: PCT/EP2018/067599
§ 371 (c)(1),
(2) Date: Dec. 22, 2020

(87) PCT Pub. No.: WO2020/001785
PCT Pub. Date: Jan. 2, 2020

(65) Prior Publication Data
US 2021/0259897 A1    Aug. 26, 2021

(51) Int. Cl.
*A61F 13/84* (2006.01)
*G01J 5/00* (2022.01)
*G06T 7/00* (2017.01)
*A61F 13/15* (2006.01)
(Continued)

(52) U.S. Cl.
CPC ........ *A61F 13/84* (2013.01); *A61F 13/15203* (2013.01); *A61F 13/4756* (2013.01);
(Continued)

(58) Field of Classification Search
CPC ............... A61F 13/84; A61F 13/15203; A61F 13/4756; A61F 13/532; A61F 13/49001;
(Continued)

(56) References Cited

U.S. PATENT DOCUMENTS 8,979,815 B2 * 3/2015 Roe ........................ A61F 13/538
604/385.01
2014/0163500 A1 * 6/2014 Roe .................... A61F 13/49001
604/374

(Continued)

FOREIGN PATENT DOCUMENTS

EP          3403631        2/2019
WO      2014093128 A1     6/2014
(Continued)

OTHER PUBLICATIONS

International Search Report and Written Opinion for PCT/EP2018/067599, dated Mar. 4, 2019.

*Primary Examiner* — Nathaniel T Woodward
*Assistant Examiner* — Philip L Cotey
(74) *Attorney, Agent, or Firm* — VIVICAR Law, PLLC

(57) ABSTRACT

A method for measuring airflow through a channel comprised in an absorbent article core, said method comprising the steps of: providing an absorbent core adapted to be sandwiched between a liquid permeable topsheet and a liquid impermeable backsheet of an absorbent article, wherein the absorbent core comprises at least one channel; providing a thermal imaging camera; loading the absorbent core with a warm liquid, wherein said warm liquid has a temperature of greater than 30° C.; simultaneously visually recording said absorbent core with said thermal imaging camera, and spraying said channel(s) with a cold fluid, wherein the cold fluid has a temperature of less than 10° C.

20 Claims, 13 Drawing Sheets

(51) Int. Cl.
*A61F 13/532* (2006.01)
*A61F 13/475* (2006.01)
*A61F 13/49* (2006.01)

(52) U.S. Cl.
CPC .............. *A61F 13/532* (2013.01); *G01J 5/00* (2013.01); *G06T 7/001* (2013.01); *A61F 13/49001* (2013.01); *A61F 2013/15552* (2013.01); *A61F 2013/8491* (2013.01); *G01J 2005/0077* (2013.01); *G06T 2207/30124* (2013.01)

(58) Field of Classification Search
CPC .... A61F 2013/15552; A61F 2013/8491; G01J 5/00; G01J 2005/0077; G06T 7/001; G06T 2201/30124
See application file for complete search history.

(56) References Cited

U.S. PATENT DOCUMENTS

| | | | |
|---|---|---|---|
| 2016/0206482 A1* | 7/2016 | Nishikawa | A61F 13/49406 |
| 2018/0027190 A1* | 1/2018 | Srinivasan | G01F 1/688 |
| | | | 348/164 |
| 2018/0066994 A1* | 3/2018 | Yee | G01P 13/04 |
| 2019/0280561 A1* | 9/2019 | Abramov | H02K 7/183 |

FOREIGN PATENT DOCUMENTS

| | | |
|---|---|---|
| WO | 2016114947 A1 | 7/2016 |
| WO | 2018122117 A1 | 7/2018 |

* cited by examiner

METHOD FOR DETERMINING AND/OR VISUALIZING AIRFLOW THROUGH ABSORBENT CORES AND ABSORBENT ARTICLES EXHIBITING ENHANCED AIRFLOW

CROSS-REFERENCE TO RELATED APPLICATIONS

This application is the national stage application of corresponding international application number PCT/EP2018/067599, filed Jun. 29, 2018.

TECHNICAL FIELD

The invention pertains to the technical field of absorbent hygiene products. In particular, the present invention relates to a disposable diapers, pants or sanitary napkins used to contain and retain bodily exudates and which is basically formed of an upper fluid-permeable layer (a topsheet), a lower fluid-impermeable layer (a backsheet) and an absorbent core positioned between them, in addition to an optional fastening system to keep it in its use configuration when placed on the user; optionally further comprising anti-leakage barriers, one or more transfer or distribution layers or layers that give integrity to the absorbent core, and/or elastic areas in the crotch and waist regions or in any other region of the diaper.

BACKGROUND

Nowadays, disposable absorbent articles with different configurations can be found in the market, important criteria for these products has always been absorption performance and comfort. In recent years, developments have been focused further on improving breathability of such products to limit moisture build-up and development of rashes. The latter has mostly focused on materials that improve water and vapor permeability.

Some further developments have been made on core geometry, for example as described in WO2014093128, wherein a pair of channels are added to the core. Such channels have been found beneficial to provide better cup-shaping leading to improved comfort and also provide some benefits to liquid distribution over the core.

The inventors have found out that adding structural or geometric features to the core may further impact the airflow along the top surface of the absorbent article. The latter having a positive impact towards breathability of the product.

It is common in the art to use colored liquids to examine and visualize absorption behaviors in absorbent cores. This has several disadvantages: the color can easily be seen close to the surface of the core but not in the bottom layer; moreover, the color itself may change the ion concentration of the liquid and thus the absorption behavior of the core. It further fails to provide any measurable indication of airflow over the surface of the absorbent article core.

It is thus desirable to develop a reliable, reproducible and simple/cost-effective method to determine, visualize and/or compare the airflow across an absorbent core, or the core utilization efficiency (e.g. liquid spread efficiency over the core).

It is further desirable to provide geometric features to an absorbent core that are particularly designed to enhance airflow along the top surface of the absorbent core.

SUMMARY OF THE INVENTION

In a first aspect, the disclosure relates to a method for measuring airflow through a channel comprised in an absorbent article core or an absorbent article comprising a core having one or more channels, said method comprising the steps of: providing an absorbent core adapted to be sandwiched between a liquid permeable topsheet and a liquid impermeable backsheet of an absorbent article or providing an absorbent article having an absorbent core sandwiched between a liquid permeable topsheet and a liquid impermeable backsheet, wherein the absorbent core comprises at least one channel; providing a thermal imaging camera; loading the absorbent core with a warm liquid, wherein said warm liquid has a temperature of greater than 30° C.; simultaneously visually recording said absorbent core with said thermal imaging camera, and spraying said channel(s) with a cold fluid, wherein the cold fluid has a temperature of less than 10° C.

In a second aspect, the present disclosure relates to an absorbent article comprising an absorbent core sandwiched between a liquid permeable topsheet and a liquid impermeable backsheet, wherein said core comprises one or more channels characterized in that the speed of airflow through the channel is greater than 200 mm/s preferably from 500 mm/s to 20,000 mm/s, more preferably from 1,000 mm/s to 15,000 mm/s, even more preferably from 2,000 mm/s to 10,000 mm/s, according to the method herein, preferably wherein said channel is in the form of a single U-shaped channel comprising two diverging end points two linear sections extending parallel to each other and each positioned between said diverging ends and a U-bend wherein the U-bend connects to each of said linear sections, and typically wherein the channel has a width of no more than 25 mm, preferably no more than 20 mm, even more preferably from 5 mm to 15 mm. Wherein typically the linear sections extend along at least 50% of the total length of the core along a length axis L and wherein the distance between the diverging end points along a transverse axis perpendicular to the length axis L is greater than the distance between two opposite points of the U-bend furthest to each other along said transverse axis.

In a third aspect, the present disclosure relates to a method for comparing liquid distribution between two or more different absorbent article cores or absorbent articles comprising an absorbent core, said method comprising the steps of: providing a first absorbent core adapted to be sandwiched between a liquid permeable topsheet and a liquid impermeable backsheet of an absorbent article, preferably wherein said first absorbent core comprises at least one channel; providing a second absorbent core adapted to be sandwiched between a liquid permeable topsheet and a liquid impermeable backsheet of an absorbent article, preferably wherein the second absorbent core comprises at least one channel; providing a thermal imaging camera; loading the first and second absorbent cores with an equal and predetermined amount of warm liquid, wherein said warm liquid has a temperature of greater than 30° C.; visually recording said absorbent core with said thermal imaging camera; and comparing an image of the first absorbent core with an image of the second absorbent core taken no more than 60 seconds from complete loading of said absorbent cores.

DETAILED DESCRIPTION OF THE INVENTION

Figure 1:
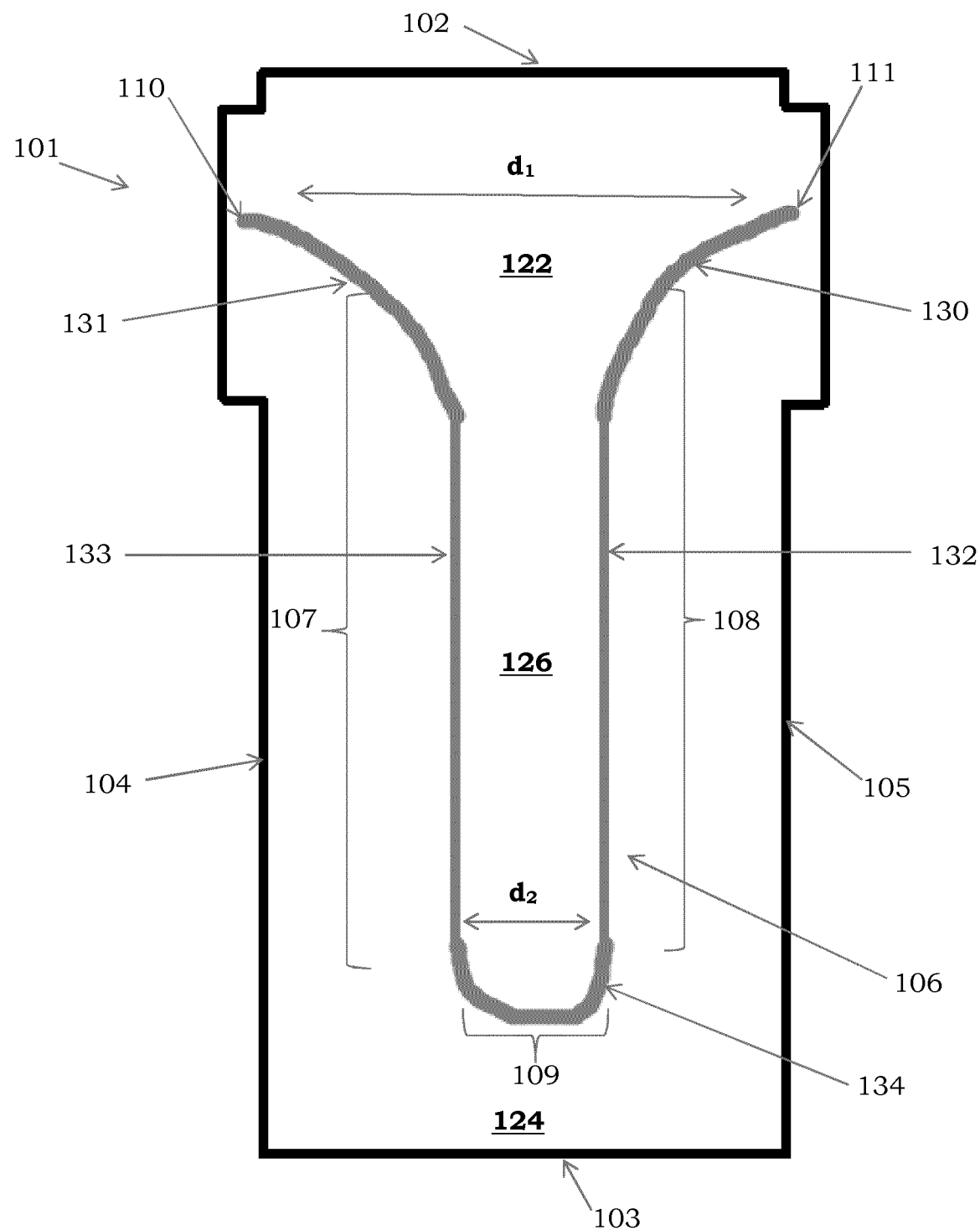
FIG. 1 shows a diagrammatic top view of an absorbent core according to an embodiment herein.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, and the like. Absorbent articles preferably comprise a longitudinal axis and a transversal axis perpendicular to said longitudinal axis. The longitudinal axis is hereby conventionally chosen in the front-to-back direction of the article when referring to the article being worn.

As used herein, the "skin-facing" or "bodyside" surface means that surface of the article or component which is intended to be disposed toward or placed adjacent to the body of the wearer during ordinary use, while the "outward", "outward-facing" or "garment-facing" surface is on the opposite side, and is intended to be disposed to face away from the wearer's body during ordinary use. Such outward surface may be arranged to face toward or placed adjacent to the wearer's undergarments when the absorbent article is worn.

"Complete loading" as used herein means the condition of the absorbent core when the entire predetermined amount of warm liquid has been absorbed by the core (e.g. the moment where no more liquid is present in the water column or pipe used to feed the liquid to the core).

The terms "different absorbent article cores" as used herein means an absorbent article, and/or absorbent article core, that comprise at least one feature which is not present in the other absorbent article. This could be for example the presence or absence of a channel, channels of differing shape, differing topsheet nonwoven layer/surfaces etc.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "elasticized" or "elastified" refers to a material, layer, or substrate that is naturally non-elastic, but which has been rendered elastic by, for example, suitably joining an elastic material, layer, or substrate thereto.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like. When used in the singular, it can have the dual meaning of a single element or a plurality of elements.

Absorbent Core

Absorbent cores herein typically comprise an absorbent material (herein also referred to as three-dimensional absorbent material) comprising a fibrous material (such as cellulose fibers and/or synthetic fibers) and/or superabsorbent polymer particles. The cores herein comprise one or more channels 106 substantially free of absorbent material, preferably wherein said channel is in the form of a single U-shaped channel comprising two diverging ends 130, 131, two linear sections 132, 133 extending parallel to each other and each positioned between said diverging ends 130, 131 and a U-bend 134, wherein the U-bend 134 connects to each of said linear sections 130, 131, such that said two diverging ends 130, 131, two linear sections 132, 133, and U-bend 134 are in fluid communication with each other, and typically wherein the channel 106 has a width of no more than 25 mm, preferably no more than 20 mm, even more preferably from 5 mm to 15 mm.

Absorbent cores 101 according to an embodiment of the present disclosure comprise: a front portion 122; a back portion 124; a crotch portion 126 position between the front portion 122 and the back portion 124; and a longitudinal axis extending along a length of said core 101 and crossing said front, crotch and back portions 122, 126, 124, the absorbent core 101 having a width extending perpendicular to said length and a perimeter comprising at least two opposing ends 102, 103 and at least two opposing sides 104, 105 positioned between said ends 102, 103 wherein the absorbent core 101 comprises one or more substantially interconnected channels 106 extending through at least a portion of the crotch portion 126 (preferably being at least 60%, more preferably at least 70%, even more preferably at least 80%, of a crotch portion length running substantially parallel to the longitudinal axis) along the length of the core and along at least a portion of said width of the core, typically along and substantially parallel to the longitudinal axis, and from one side of the core [e.g. a first side 104] to the other [e.g. a second side 105], preferably said one or more substantially interconnected channels 106 being symmetric or asymmetric about the longitudinal axis. An advantage of such interconnected channel arrangement is that faster immediate distribution of fluid is achieved across the core versus a core free of such interconnected channels or cores comprising only discontinuous channels. Such contributes to limit oversaturation of the core in the portion of fluid discharge. Without wishing to be bound by theory it is believed that the fact that the fluid is distributed across the core and immediately away from the fluid discharge position, a perception of dryness and skin comfort is provided to the subject, as well as an impression of longer lasting dryness by the user.

Figure 11:
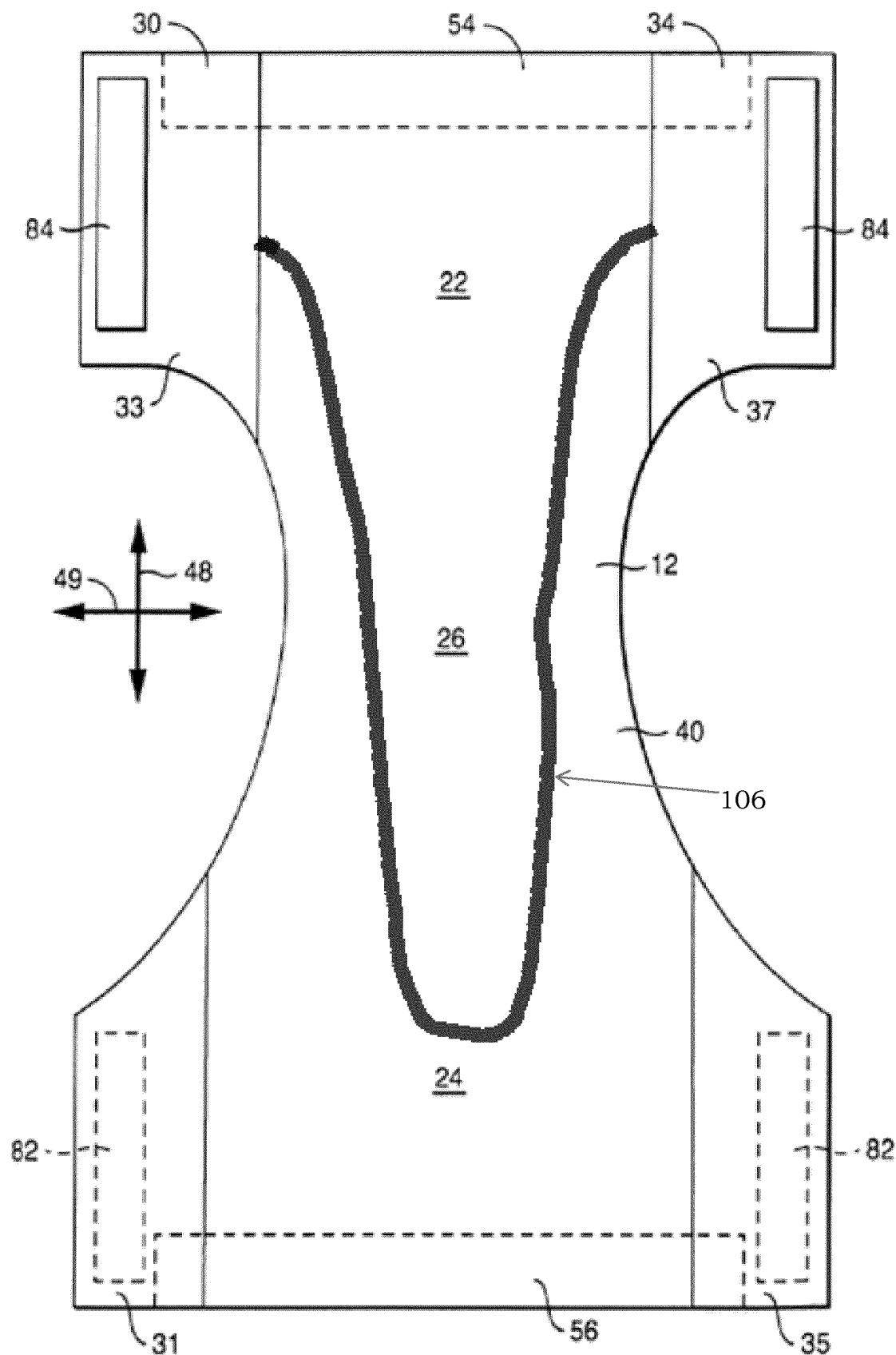
FIG. 11 shows a plan view of an absorbent article according to an embodiment herein.
Figure 12:
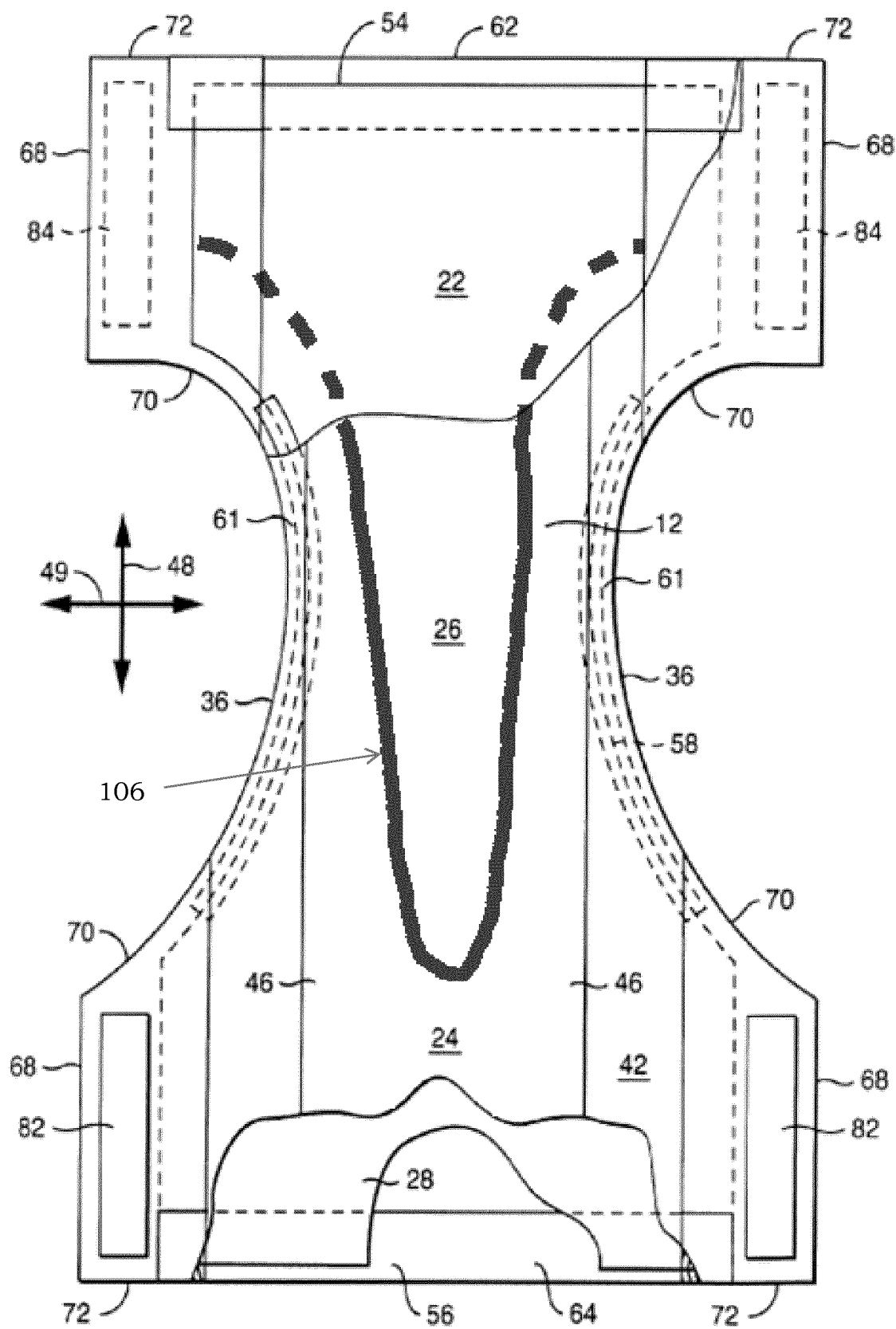
FIG. 12 shows a plan view of an absorbent article according to an embodiment herein.
Figure 13:
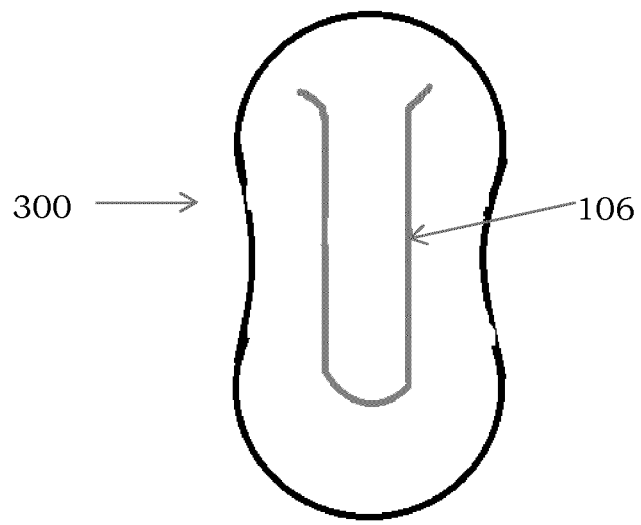
FIG. 13 shows a diagrammatic view of an absorbent article according to an embodiment herein.
Figure 14:
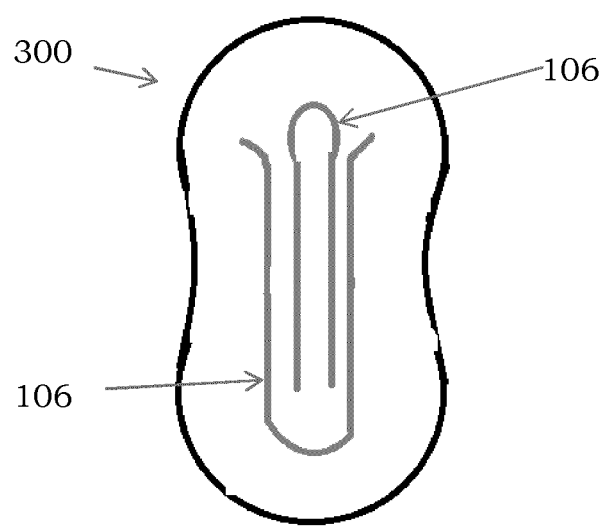
FIG. 14 shows a diagrammatic view of an absorbent article according to an embodiment herein.

The longitudinal axis of the core referred to herein may be substantially parallel to the longitudinal direction 48 (as illustrated for example in FIG. 11 and FIG. 12), and the width of the core or width axis of the core referred to herein may be substantially parallel to the lateral direction 49 (as illustrated for example in FIG. 11 and FIG. 12).

In an embodiment the one or more interconnected channels are shaped such to effectively conduct fluid away from a region of discharge, typically by forming a shape that has a distance gradient between opposing surfaces of the interconnected channels, preferably forming a funnel-shaped profile.

Figure 4:
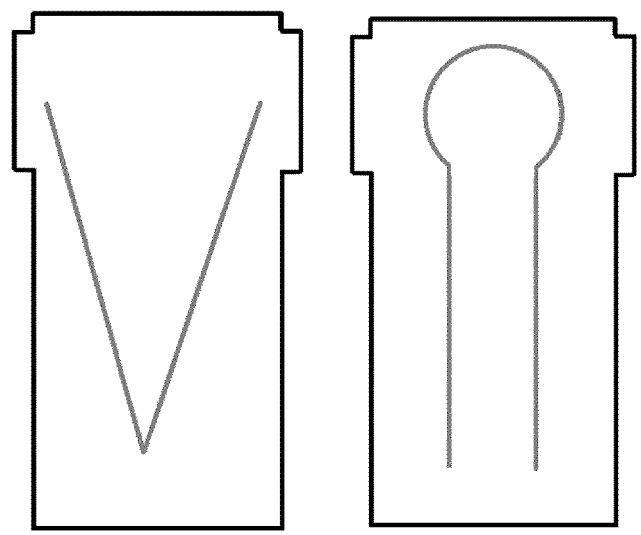
FIG. 4 shows a diagrammatic top view of absorbent cores according to an embodiment herein and having different geometrical shapes formed by interconnected channels.
Figure 4:
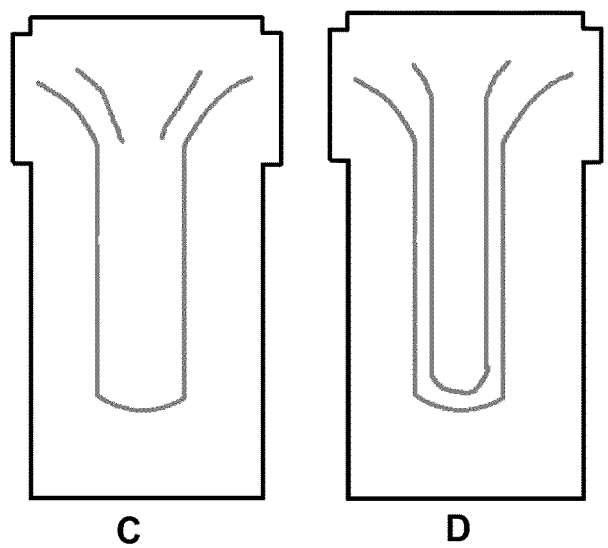
Figure 4:
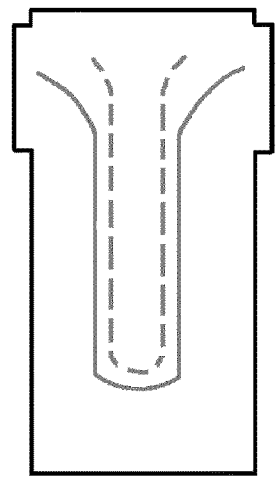
Figure 5:
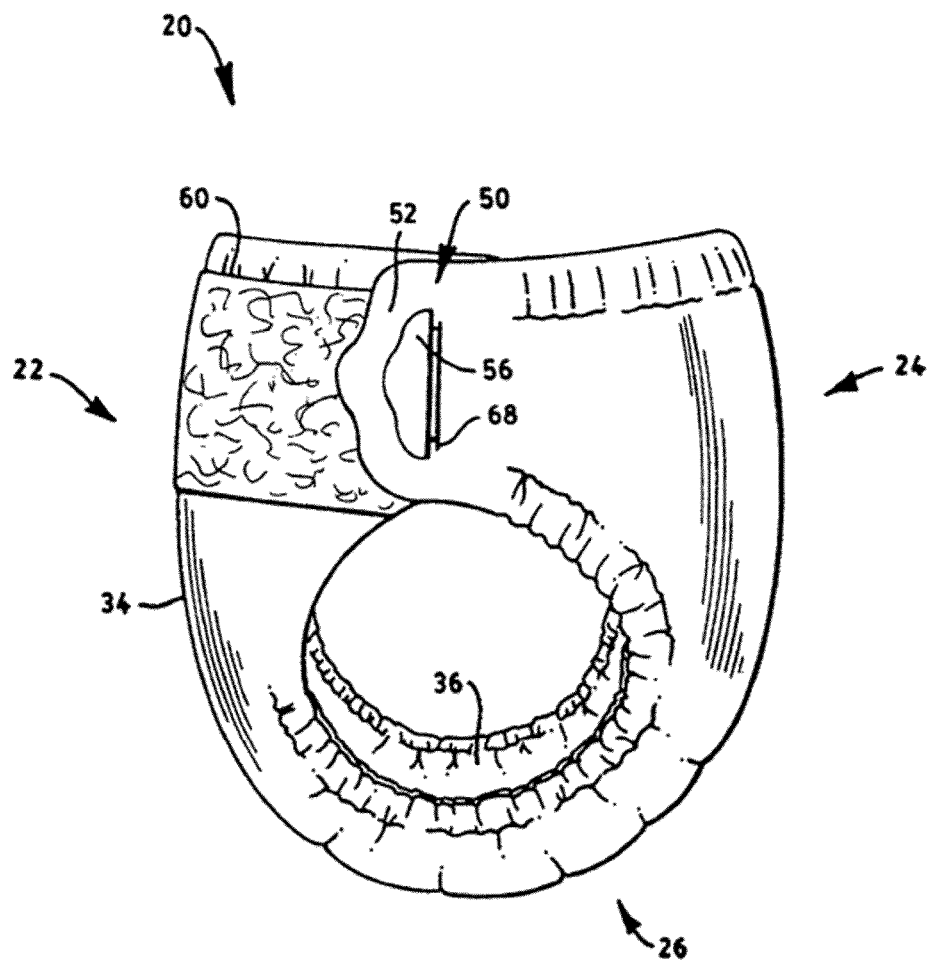
FIG. 5 shows a perspective overview of an absorbent article according to an embodiment herein.
Figure 6:
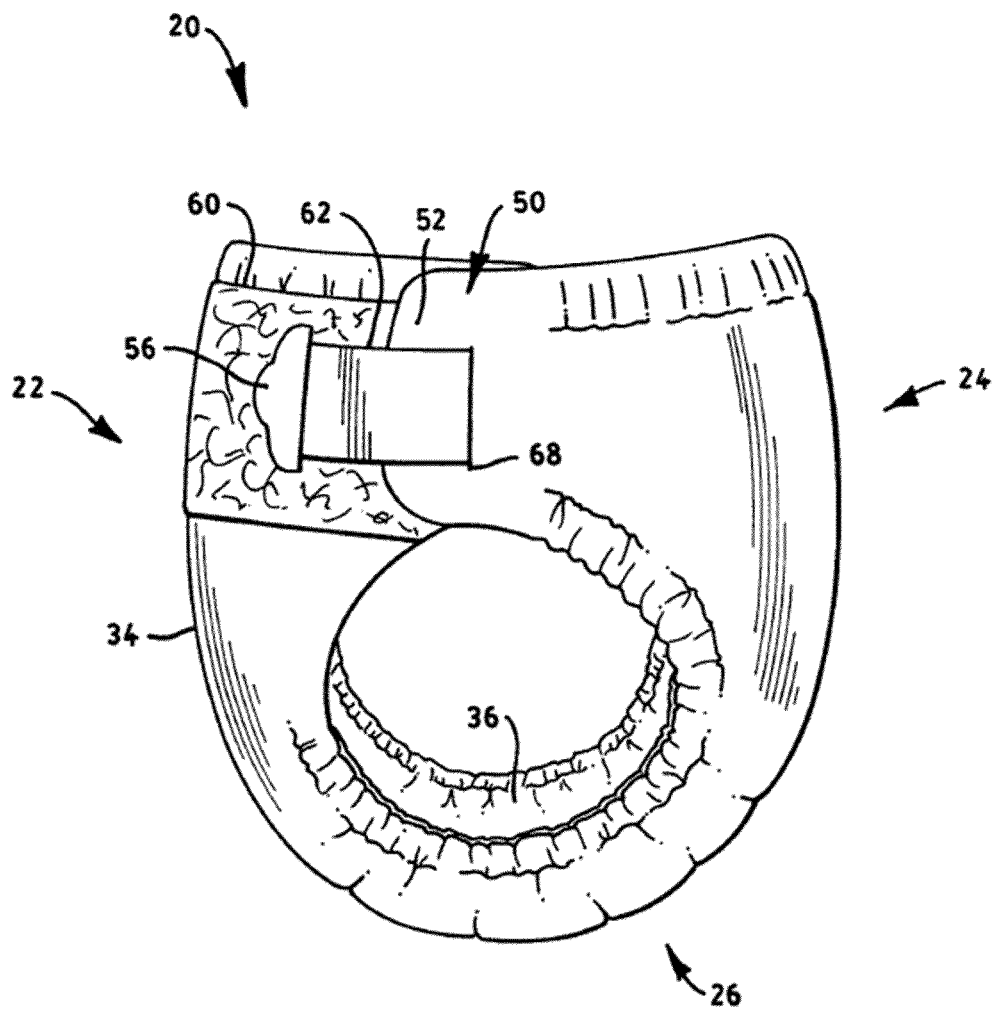
FIG. 6 shows a perspective overview of a product according to an embodiment herein.
Figure 7:
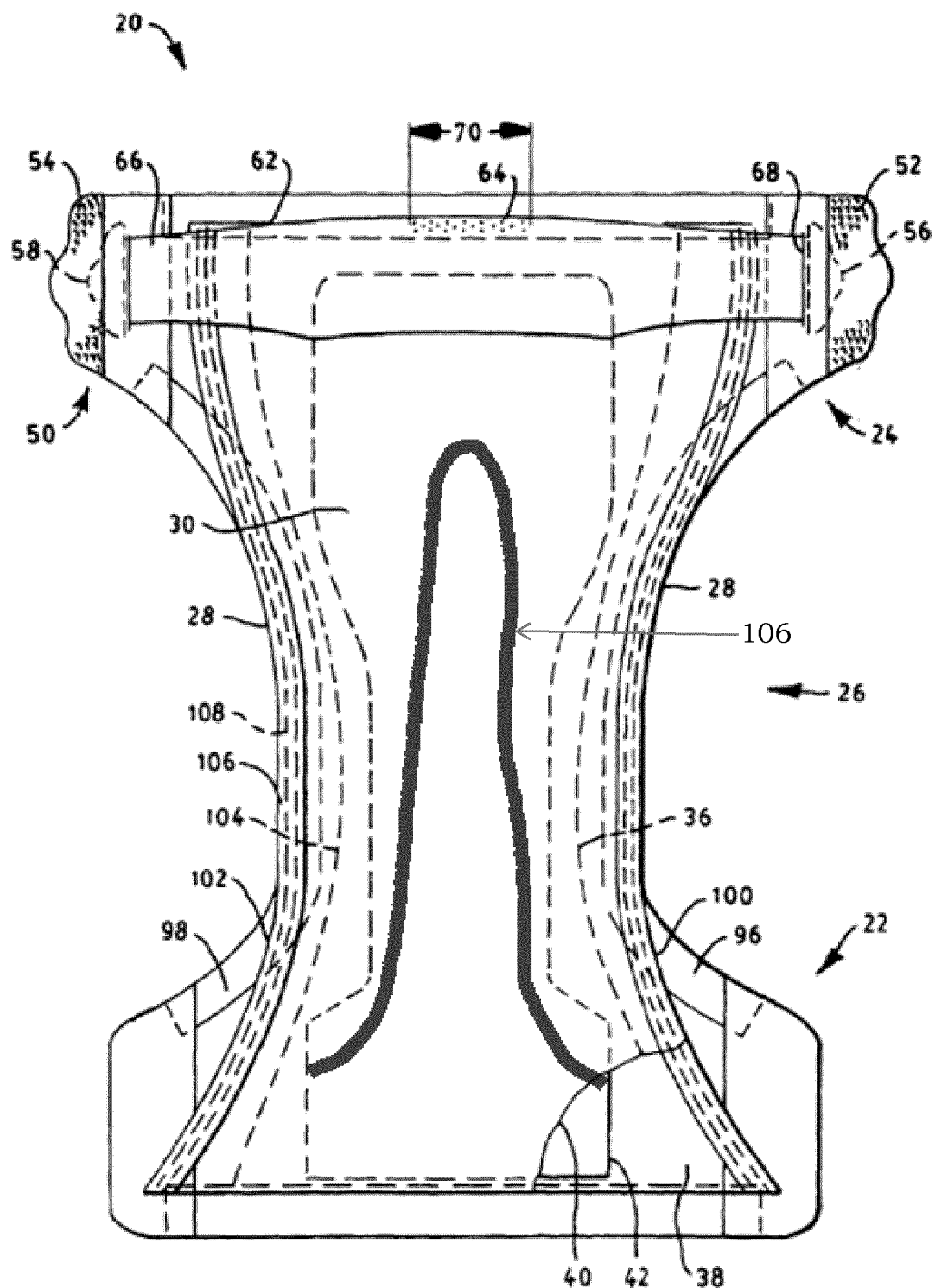
FIG. 7 shows a plan view of an absorbent article according to an embodiment herein.
Figure 8:
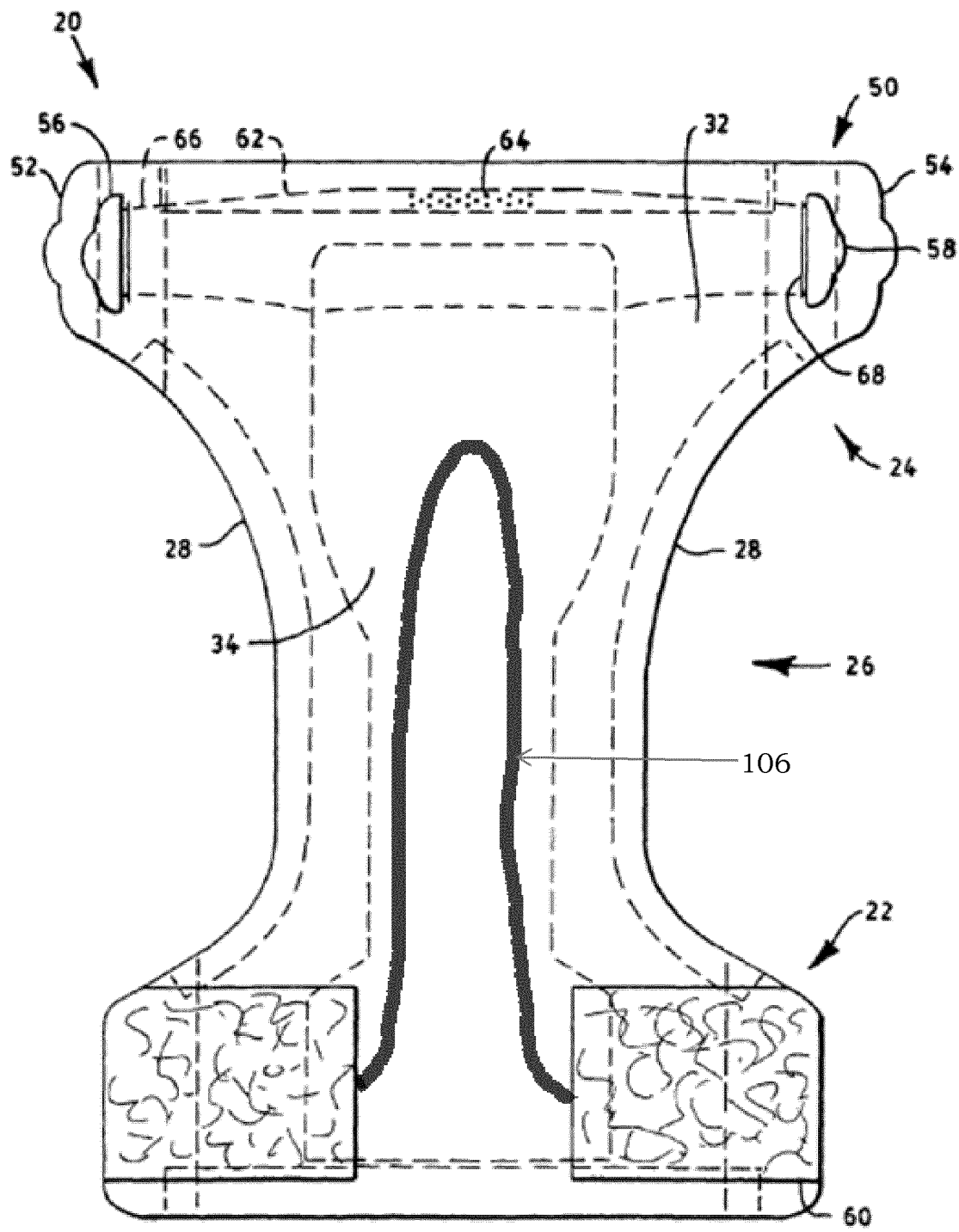
FIG. 8 shows a plan view of an absorbent article according to an embodiment herein.
Figure 9:
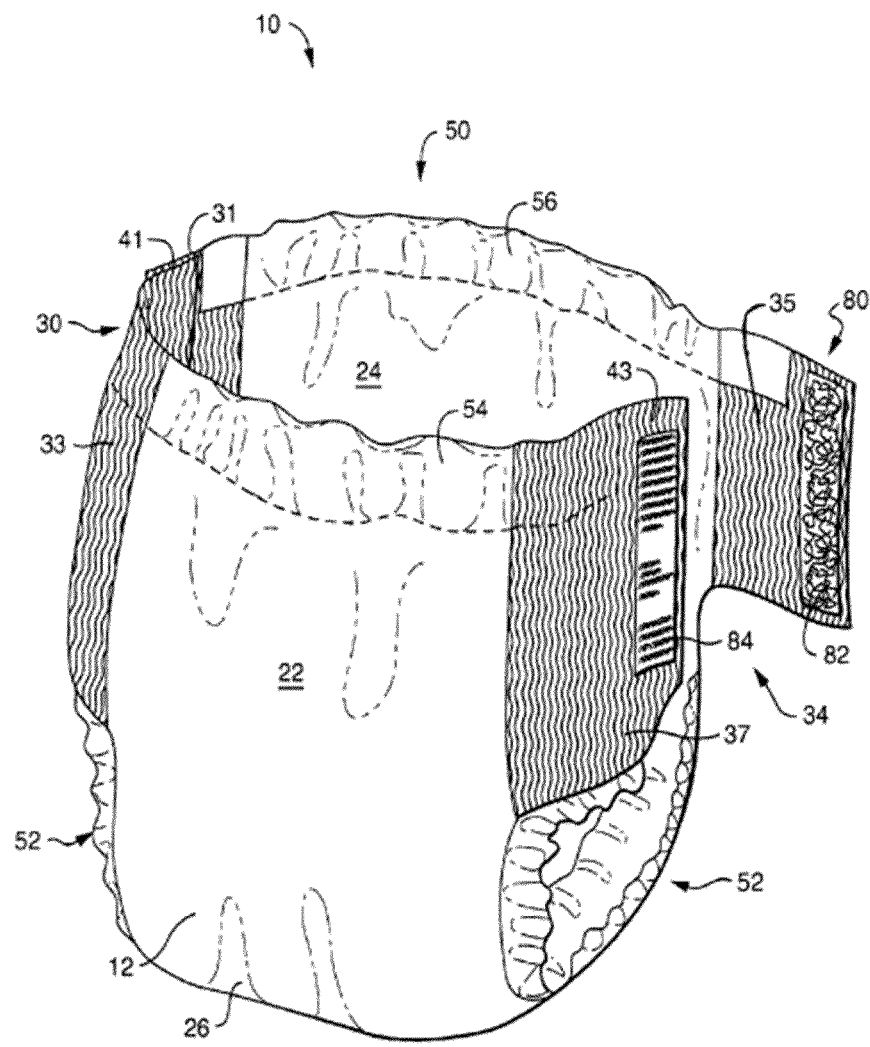
FIG. 9 shows a perspective overview of an absorbent article according to an embodiment herein.
Figure 10:
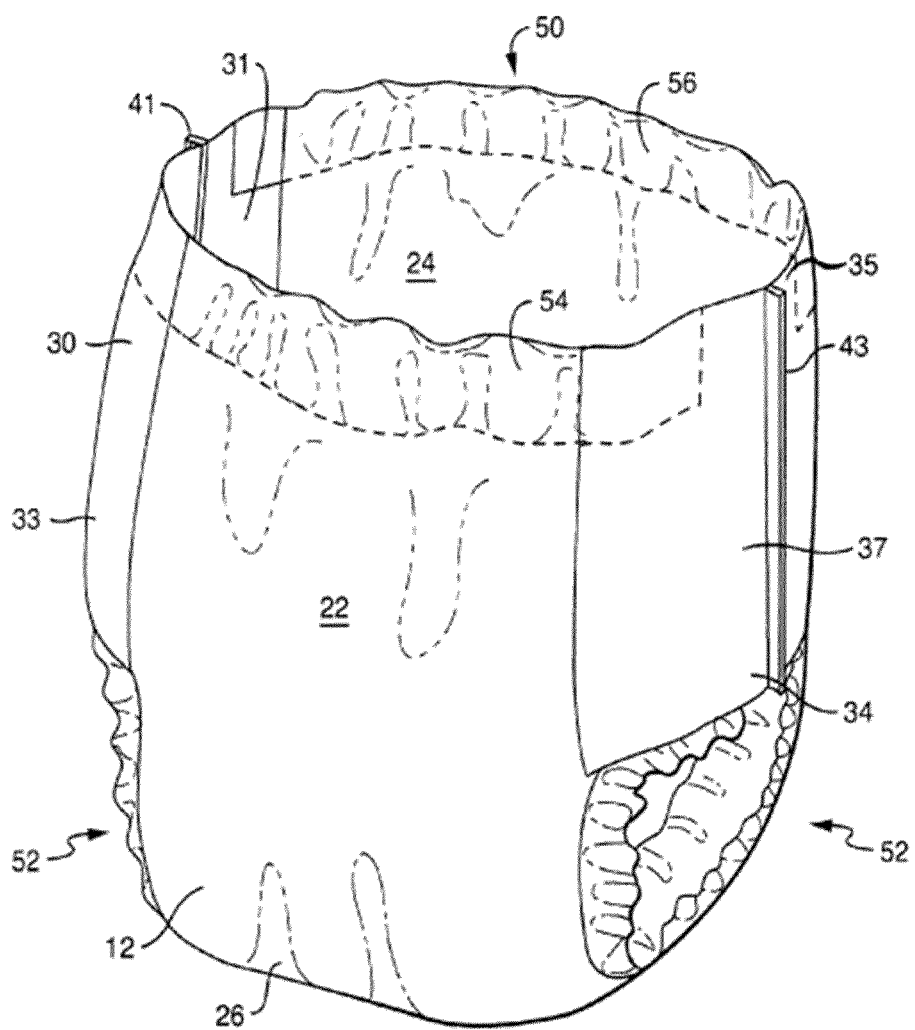
FIG. 10 shows a perspective overview of a product according to an embodiment herein.

In an embodiment, the channels form a geometric shape across the absorbent core and along a plane extending parallel to the longitudinal axis of said core, said geometric shape being selected from the group consisting of a semi-hourglass-shaped, v-shaped, u-shaped, pie-shaped, and combinations thereof. Wherein "by semi-hourglass-shaped" it is intended an hourglass shape with only a single end, exemplary shapes are shown in FIG. 4.

In an embodiment, the channels comprise, preferably consist of, a first nonwoven web bonded to a second nonwoven web by one or more adhesives. Preferably, the adhesive is applied in zones across the width of the channels such to form zones, preferably alternating zones, of different bonding strength between the nonwoven web laminate. For example the first nonwoven web may be bonded to the second nonwoven web on at least three zones along the width of the channel. Such arrangement may comprise a first adhesive zone, a second adhesive zone and a third adhesive zone, the second adhesive zone being interposed between the first and third adhesive zones along the width of the channel (e.g. at an axis parallel to the core width and perpendicular to the longitudinal axis of the core) wherein the bonding strength of the second adhesive zone is greater than the bonding strength of the first and third adhesive zones. Examples of ways to achieve such stronger bonding strength in the second zone include using higher amounts of adhesive in this zone, applying greater mechanical pressure on this zone, or utilizing a different adhesive type, other ways are also contemplated provided a stronger adhesion between nonwoven webs results in such region.

In an embodiment the bonding strength in the first and third zones is less than the tensile force generated by the absorbent material located proximal to the channel upon wetting, such that the first and second nonwoven webs may separate in said zones; and wherein the bonding strength in the second zone is greater than the tensile force generated by the absorbent material located proximal to the channel upon wetting, such that the first and second nonwoven webs may not separate in said zone upon wetting and typically the swelling of the absorbent material, and rather may remain fixedly joined. An advantage of this arrangement is that in dry conditions a noticeable channel is visible from the topsheet side of the article and/or core providing broad channels that are further useful for channeling more fluid particularly at initial/early discharge. This arrangement then further allows the bonding at the first and third regions to fail upon for example swelling of the SAP such to allow more volume to be available for expansion thereof (and prevent early saturation or non-optimal absorption), with typically the second zone resisting such expansion and thus providing integrity of the channels even in wet state.

In a preferred embodiment the first nonwoven web and/or the second nonwoven web, preferably the second nonwoven web, are elastic nonwovens (e.g. containing an elastic material such as Vistamaxx resin from ExxonMobil, or other suitable polymers capable of imparting elasticity to a nonwoven web). An advantage of this embodiment is that the nonwoven web better and more easily wraps around the 3D insert upon application of a vacuum and permits subsequent joining to the first nonwoven web at a location corresponding to a position of the base of the 3D insert (opposite a protruding apex thereof). This has an advantage of limiting the formation of fluid collection basins or sinks within the channels.

Figure 2:
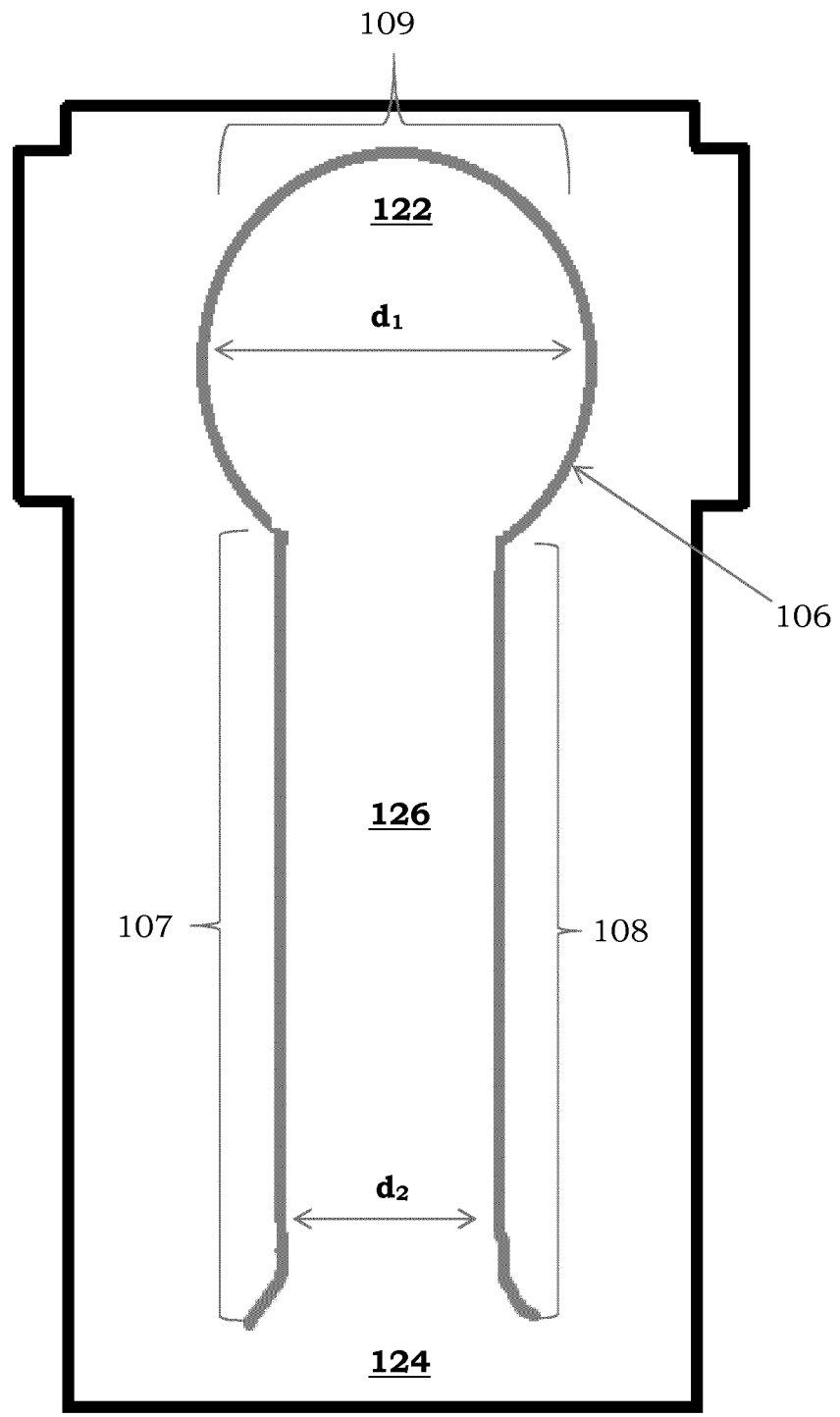
FIG. 2 shows a diagrammatic top view of an absorbent core according to an embodiment herein.
Figure 3:
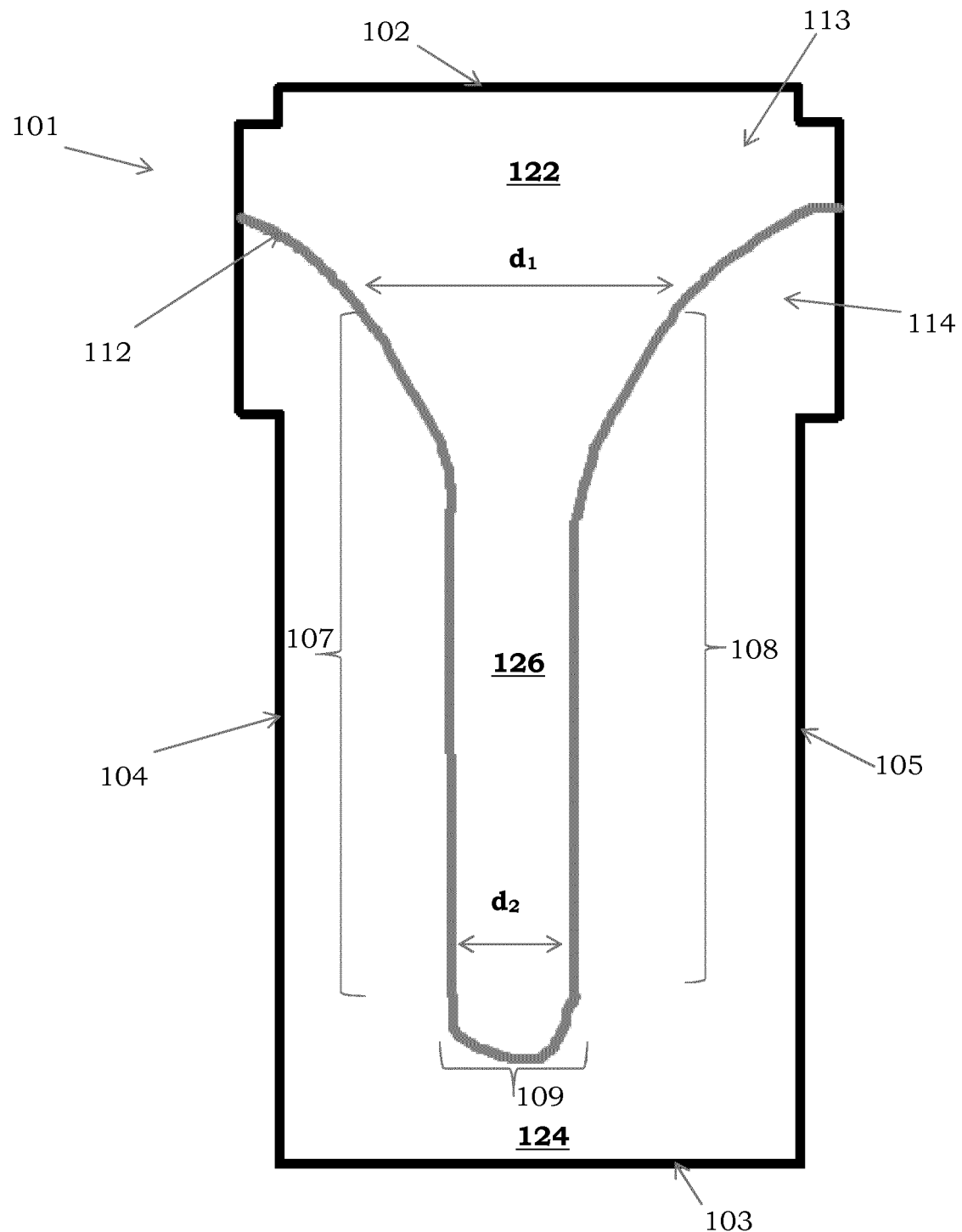
FIG. 3 shows a diagrammatic top view of an absorbent core according to an embodiment herein.

In an embodiment, referring to FIG. 1 to FIG. 3, at least one and preferably each substantially interconnected channel 106 comprises: a first channel portion 107 extending substantially along the longitudinal axis proximal to a first side 104 of the core 101; a second channel portion 108 extending substantially along the longitudinal axis proximal to a second side 105 of the core 101; and at least one, preferably only one, connecting channel portion 109 in fluid communication with said first and second channel portions 107, 108. An advantage of this arrangement is fast liquid distribution along more than one axis of the absorbent core, typically both the longitudinal axis and the width axis thereof, such to maximize the absorption capabilities of the absorbent core over its entire surface area. Moreover, such geometry improves the folding of the core and thus allows for a better and snug fit onto the subjects skin (with or without addition of further elastics proximal to said channel portions).

Hereby, connecting channel portion 109 of at least one of the interconnected channels, the connecting channel portion being in fluid communication with said first and second channel portions 107, 108, preferably forms said closed end in the form of a U-bend, preferably wherein the first and second channel portions 107, 108 diverge away from the longitudinal axis at least along a portion of the interconnecting channel 106 typically exiting from the U-bend, thereby at least partially forming a funnel-shaped interconnected channel near the closed end.

The first and second channel portions may be substantially linear; or have a substantially curved profile preferably selected from concave or convex; or may comprise a combination of said linear and curved profiles. In a preferred embodiment, the first and second channel portions are concave in shape and are generally symmetric about at least the longitudinal axis.

The first and second channel portions may extend through at least a majority, preferably the entirety, of the length of the crotch portion along the longitudinal axis and typically run substantially parallel to the sides of the core forming the perimeter thereof.

In a highly preferred embodiment, each interconnected channel herein comprises only a single connecting channel portion 109, typically forming an apex of the inter connected channel. An advantage of this embodiment is fast fluid distribution through the core whilst limiting the risk of blockages that could otherwise result if pockets of wetted areas are rather formed.

Preferably, the connecting channel portion 109 extends substantially along the width of said core 101, preferably forming a closed end within a surface of said core 101 along a plane parallel to the longitudinal axis, and preferably positioned opposite to an open end formed by non-connected first and second terminal positions 110, 111 of the interconnected channel 106, preferably of the first and second channel portions 107, 108 respectively, typically said non-connected first and second terminal positions 110, 111 being distal to each other and proximal to the first and second sides 104, 105 of said core 101 respectively, even more preferably said terminal positions 110, 111 facing away from each other such to form a funnel-shaped geometrical opening therebetween. Without wishing to be bound by theory it is believed that such geometry aids to "funnel" and collect more fluid where it is needed and quickly and effectively distribute it away from the region of collection.

In an embodiment, and preferably in combination with the previous embodiment, the interconnected channel comprises unconnected first 110 and second 111 terminal positions, whereby the first terminal position 110 extends to a first side 104 of the core and/or the second terminal position 111 extends to a second side 105 of the core, as for instance illustrated in FIG. 3. Hereby the entire width of the absorbent core can be covered by the channel, which ensures a better fluid distribution.

In an embodiment, the closed end is substantially curvilinear in shape, preferably forming a convex shape between the first and second channel portions 107, 108, or is substantially linear in shape, preferably forming a straight or triangular shape between the first and second channel portions 107, 108. The closed end may be formed by the connecting channel portion 109. An advantage of such shape is increasing the surface area of contact with neighboring regions of three-dimensional absorbent material such to better promote absorption of the distributed liquid once evacuated from areas of typically high saturation.

In an embodiment, a first distance (d1) between the first channel portion 107 and the second channel portion 108, a second distance (d2) between the first channel portion 107 and the second channel portion 108, wherein the first distance (d1) is proximal to the front portion 122 of the core 101 and the second distance (d2) is proximal to the back portion 124 of the absorbent core 101, and wherein the first distance (d1) is greater than the second distance (d2), preferably wherein the first distance (d1) is at least 1.5d2, more preferably from 1.8d2 to 3d2. An advantage being the fast and effective fluid distribution from regions of typically high saturation towards regions of typically lower saturation.

In an embodiment, the core comprises a first nonwoven web, typically in the form of a backsheet; a second nonwoven web, typically in the form of a topsheet; and a three-dimensional absorbent material positioned between the first and second nonwoven webs to form an absorbent core laminate, typically wherein the three-dimensional absorbent material comprises a fibrous web typically comprising airlaid fibers, and preferably comprises a predetermined amount of super absorbent polymer dispersed therethrough.

In a highly preferred embodiment, the interconnected channel 106 is substantially free of three-dimensional absorbent material, and preferably also free of super absorbent polymer. Without wishing to be bound by theory it is believed that absorbent materials delay fluid distribution compared to the effectiveness of such channels, indeed as fluid is absorbed by the absorbent materials they swell and/or saturate effectively reducing the amount of fluid that could be allowed to travel therethrough. Eliminating such materials from the channels allows to maintain a highly efficient fluid distribution system that operates substantially independently from the fluid acquisition/absorption mechanism of the neighboring regions.

In a preferred embodiment, the core comprises a plurality of substantially interconnected channels, preferably arranged in a substantially concentric manner, an example being shown in FIG. 4E. An advantage being the exponential effectiveness in liquid distribution and channel formation, particularly as neighboring regions become more saturated or swell.

In an embodiment, as shown in FIGS. 4C and 4D, the core further comprises one or more disconnected channels, preferably at least a portion thereof being arranged concentrically to the substantially interconnected channel. An advantage being effective added local uniform fluid distribution. Moreover, it is believed that upon swelling of the neighboring regions to the channels, upon saturation, visual patterns may be formed that more evidently convey the perception of efficacy of the entire core surface for absorption of fluid.

Preferably, the substantially interconnected channels 106 have a regular or irregular depth, said depth being measured on an axis perpendicular to both the longitudinal axis and the axis along the width of the core 101, preferably wherein the cross-section of said channels 106 is selected from the group consisting of curved, polygonal or combinations thereof.

In a preferred embodiment, as illustrated in FIG. 16, the width of the interconnected channel 106 may vary along the channel. Preferably, the width of the channel decreases from the terminal positions 110, 111 towards the connecting channel portion 109. This is illustrated in FIG. 16, wherein the width 210a of the channel 106 near the first terminal position 110 and the width 210b of the channel 106 near the second terminal position 111 are larger than the width 211a of the channel 106 in the first channel portion 107 and the width 211b of the channel 106 in the second channel portion 108, which are larger than the width 212 of the channel 106 in the connecting channel portion 109. Such variance of the width of the channel portions leads to faster distribution. Without wishing to be bound by theory, the inventors believe that the varying width leverages capillary effects that better promote liquid transport from the front to the back of the absorbent article.

It is understood that a number of alternative shapes may be used for channels described herein, examples of which are shown in FIG. 4 and FIG. 16 without departing from the disclosure embodiments described herein.

Absorbent Article

Absorbent articles 10, 20, 300 herein are preferably of the disposable type and comprise an absorbent core 101 sandwiched between a liquid permeable topsheet 40 and a liquid impermeable backsheet 38, wherein said core 101 comprises one or more channels 106 characterized in that the speed of airflow through the channel 106 is greater than 200 mm/s preferably from 500 mm/s to 20,000 mm/s, more preferably from 1,000 mm/s to 15,000 mm/s, even more preferably from 2,000 mm/s to 10,000 mm/s, according to the method of described herein, preferably wherein said channel 106 is in the form of a single U-shaped channel comprising two diverging ends 130, 131 two linear sections 132, 133 extending parallel to each other and each positioned between said diverging ends 130, 131 and a U-bend 134, wherein the U-bend 134 connects to each of said linear sections 130, 131 such that said two diverging ends 130, 131, two linear sections 132, 133, and U-bend 134 are in fluid communication with each other, and typically wherein the channel 106 has a width of no more than 25 mm, preferably no more than 20 mm, even more preferably from 5 mm to 15 mm.

The absorbent article may comprise an absorbent core of any of the previously described embodiments in the "absorbent core" section hereinabove.

In an embodiment, the absorbent article may comprise further components selected from: one or more leg elastics 96,98; one or more liquid impermeable containment flaps; one or more stretchable side panels 30,34; one or more fastening components 82,84; back and/or front elastic waistbands 56,54; a liquid distribution layer (ADL); and combinations thereof.

Airflow Measurement

The method is for measuring airflow through a channel comprised in an absorbent article core or absorbent article comprising said core, said method comprising the steps of: providing an absorbent core adapted to be sandwiched between a liquid permeable topsheet and a liquid impermeable backsheet of an absorbent article, wherein the absorbent core comprises at least one channel; providing a thermal imaging camera; loading the absorbent core with a warm liquid, wherein said warm liquid has a temperature of greater than 30° C.; simultaneously visually recording said absorbent core with said thermal imaging camera, and spraying said channel(s) with a cold fluid, wherein the cold fluid has a temperature of less than 10° C. It has been found that such a method allows to very quickly and effectively compare airflow capabilities of absorbent articles in a visual manner that may also serve as live demonstrations of airflow capabilities of a core (positively impacting also the overall breathability of the article).

In an embodiment, the method further comprises the step of preconditioning the absorbent core at room conditions for at least two hours, typically wherein room condition is at a temperature of 23° C. to 1° C. and relative humidity 50% to 2%, preferably said preconditioning step being before the loading step.

Preferably, the warm liquid has a temperature of greater than 35° C., preferably from 36° C. to 40° C., even more preferably from 37° C. to 38° C.

Preferably the cold fluid has a temperature of less than 5° C., preferably from −20° C. to 3° C., more preferably from −10° C. to 2° C., more preferably from −5° C. to 1° C., even more preferably from −3° C. to 0° C.

Preferably the cold fluid consists of a liquefied gas preferably selected from the group consisting of propane, butane, and mixtures thereof.

Preferably the absorbent article is a personal hygiene article selected from disposable diapers and/or pants, sanitary napkins, and combinations thereof.

Preferably the cold fluid is sprayed at a single position for each channel. Typically the spray is applied at a vertical distance of at least 5 cm from the uppermost surface of the absorbent core.

Preferably the warm liquid comprises a salt at an amount of from 0.5% wt to 1.5% wt, preferably wherein the salt comprises sodium chloride, preferably consists of a 0.9% saline solution.

In a preferred embodiment, a distance measuring scale is position proximal to the channel and extending parallel thereto, and the method further comprising the step of recording the time following the spraying step such that the speed of airflow through the channel is measured.

Liquid Distribution Measurement

The method is for comparing liquid distribution between two or more different absorbent article cores, said method comprising the steps of: providing a first absorbent core adapted to be sandwiched between a liquid permeable topsheet and a liquid impermeable backsheet of an absorbent article, preferably wherein said first absorbent core comprises at least one channel; providing a second absorbent core adapted to be sandwiched between a liquid permeable topsheet and a liquid impermeable backsheet of an absorbent article, preferably wherein the second absorbent core comprises at least one channel; providing a thermal imaging camera; loading the first and second absorbent cores with an equal and predetermined amount of warm liquid, wherein said warm liquid has a temperature of greater than 30° C.; visually recording said absorbent core with said thermal imaging camera; and comparing an image of the first absorbent core with an image of the second absorbent core taken no more than 60 seconds from complete loading of said absorbent cores.

Preferably, the comparing step comprises the step of comparing the surface area of each image highlighting regions having temperature of greater than 25° C., preferably greater than 27° C.

The comparing step may alternatively or further comprise the steps of: converting each said image in black and white and for each image run an image analysis to count the total number of black pixels in the image; and comparing the total number of black pixels of said images.

Preferably, the warm liquid has a temperature of greater than 35° C., preferably from 36° C. to 40° C., even more preferably from 37° C. to 38° C.

EXAMPLES

Example 1— Liquid Distribution Measurement (or Liquid Spread Measurement)

Step 1: Preparing the absorbent article—The absorbent article is to be pre-conditioned at 23° C.±1° C. temperature and 50%±2% relative humidity for at least two hours. The dry absorbent article is placed flat on a hook surface, with the skin-facing side pointing upwards.

A metal weight of 3.5 kg with an integrated, transparent pipe is placed on the core: the bottom surface of the weight is a square of 100 mm length, including a cylindrical hole in the center; the pipe is 300 mm long, with an inner diameter of 20 mm. A funnel is placed on top of the pipe in order to facilitate filling the liquid into the pipe.

For placing the weight, the center point of the absorbent article is determined in both longitudinal and lateral direction. In lateral direction, the weight is placed centrally on the core. In longitudinal direction, the back edge of the weight is aligned with the center point of the article.

Step 2: Adding test liquid into the core—For the test liquid, it is preferred to use 0.9% saline solution in order to simulate the ion concentration of urine. Alternatively, tap water can be used as well although less preferred. The temperature of the liquid is chosen to be similar to human body temperature, i.e. in the range 36° C. to 38° C. The primary reason for choosing body temperature is to make the liquid visible with the thermal camera. In addition, having the same temperature as human urine, this simulates the in-use behavior of real diapers in the best possible way.

The liquid amount of 120 ml is pre-metered in a beaker. Then the beaker is emptied into the funnel in one gush.

Step 3: Visualizing the process of liquid distribution with a thermal imaging camera—Due to the temperature difference between the absorbent core and the test liquid, the process of liquid aqcuisition into the absorbent core, and the liquid distribution within the core can be visualized with a thermal imaging camera.

A suitable model is the Fluke TiS75. This camera features a resolution of 320×240 pixels for the thermal image, and includes manually adjustable focus. Moreover, it allows for both still image and video capturing.

Step 4: Determining the area of liquid spread—After the liquid has been completely absorbed by the core, the weight is removed.

The thermal camera can now be used for making the entire area of fluid spread visible. Again, a measuring scale (e.g. a ruler) is used for measuring the wet area. This can be particularly useful for comparing different types of absorbent cores, e.g. with and without channels, respectively.

Moreover, it is possible to characterize the liquid distribution inside the absorbent core, e.g. along channel structures, or due to zones of different material density: on the thermal images, it is possible to distinguish between different levels if fluid saturation, even if the liquid has been distributed within the interior layers of the absorbent core. The images may further be analyzed by converting them into black and white and comparing the percentage of black pixels between images.

Example 2— Airflow Through Core Channels

Step 1: Preparing the absorbent article—The same procedure as described in Example 1 is followed.

Step 2: Adding test liquid into the core—The same procedure as described in Example 1 is followed.

Step 3: Visualizing the air flow through the channel structure—The cold spray is a propane-butane blend (such as commercially available Synthetisches Eisspray manufactured by Aerochemica Dr. Deppe GmbH and distributed by AuxynHairol). The spray bottle is equipped with a thin pipe allowing to create a collimated stream of cold gas.

For the thermal camera, it is advantageous to use a model covering a temperature range down to at least −20° C. For instance, the Fluke TiS75 (manufactured and sold by the Fluke corporation) is a suitable choice.

The stream of cold spray is directed along the longitudinal direction of the absorbent core, essentially parallel to the surface of the article. If the core contains at least one essentially longitudinal channel, which has a pronounced shape and which has maintained its integrity after adding the liquid to the core, the spray can float through the core channel. If this effect happens, it can clearly be seen on the display of the thermal imaging camera.

By recoding the time during the spraying and placing a measuring scale (such as a ruler) next to the channel, the speed of airflow through the channel can be measured.

Although the invention submitted is described in detail in function of the preferred forms of implementation, it is not restricted to other forms of implementation and additional modifications that are within the spirit and scopes thereof.

The invention claimed is:

1. A method for measuring airflow through a channel comprised in an absorbent article core, said method comprising the steps of:
   providing an absorbent core (101) adapted to be sandwiched between a liquid permeable topsheet (40) and a liquid impermeable backsheet (38) of an absorbent article (10, 20, 300), wherein the absorbent core (101) comprises at least one channel (106);
   providing a thermal imaging camera;
   loading the absorbent core (101) with a warm liquid, wherein said warm liquid has a temperature of greater than 30° C.;
   simultaneously visually recording said liquid loaded absorbent core with said thermal imaging camera, and spraying said channel(s) (106) with a cold fluid, wherein the cold fluid has a temperature of less than 10° C.

2. A method according to claim 1 further comprising the step of preconditioning the absorbent core (101) at room conditions for at least two hours.

3. A method according to claim 1 wherein the warm liquid has a temperature of greater than 35° C..

4. A method according to claim 1 wherein the cold fluid has a temperature of less than 5° C..

5. A method according to claim 1 wherein the cold fluid consists of a liquefied gas.

6. A method according to claim 1 wherein the absorbent article is a personal hygiene article selected from disposable diapers, disposable pants, sanitary napkins, and combinations thereof.

7. A method according to claim 1 wherein the cold fluid is sprayed at a single position for each channel.

8. A method according to claim 1 wherein the warm liquid comprises a salt at an amount of from 0.5% wt to 1.5% wt.

9. A method according to claim 1 wherein a distance measuring scale is position proximal to the channel and extending parallel thereto, and the method further comprising the step of recording the time following the spraying step such that the speed of airflow through the channel is measured.

10. An absorbent article (10, 20, 300) comprising an absorbent core (101) sandwiched between a liquid permeable topsheet (40) and a liquid impermeable backsheet (38), wherein said core comprises one or more channels (106) characterized in that the speed of airflow through the channel (106) is greater than 200 mm/s according to the method of claim 9, and wherein the channel (106) has a width of no more than 25 mm.

11. A method for comparing liquid distribution between two or more different absorbent article cores, said method comprising the steps of:
providing a first absorbent core adapted to be sandwiched between a liquid permeable topsheet and a liquid impermeable backsheet of an absorbent article;
providing a second absorbent core adapted to be sandwiched between a liquid permeable topsheet and a liquid impermeable backsheet of an absorbent article;
providing a thermal imaging camera;
loading the first and second absorbent cores with an equal and predetermined amount of warm liquid, wherein said warm liquid has a temperature of greater than 30° C.;
visually recording said absorbent core with said thermal imaging camera; and
comparing an image of the first absorbent core with an image of the second absorbent core taken no more than 60 seconds from complete loading of said absorbent cores.

12. A method according to claim 11 wherein the comparing step comprises the step of comparing the surface area of each image highlighting regions having temperature of greater than 25° C..

13. A method according to claim 11 wherein the comparing step comprises the steps of: converting each said image in black and white and for each image run an image analysis to count the total number of black pixels in the image; and comparing the total number of black pixels of said images.

14. A method according to claim 11 wherein the absorbent article is a personal hygiene article selected from disposable diapers, disposable pants, sanitary napkins, and combinations thereof.

15. A method according to claim 11 wherein the warm liquid has a temperature of greater than 35° C..

16. A method according to claim 1, wherein the cold fluid consists of a liquefied gas selected from the group consisting of propane, butane, and mixtures thereof.

17. A method according to claim 1, wherein the warm liquid has a temperature of from 36° C. to 40° C.

18. A method according to claim 1, wherein the cold fluid has a temperature of from −20° C. to 3° C.

19. A method according to claim 11, wherein one or more of said first absorbent core and said second absorbent core comprises at least one channel.

20. A method according to claim 11, wherein the warm liquid has a temperature of from 36° C. to 40° C.

* * * * *